(12) United States Patent
Marano, Jr. et al.

(10) Patent No.: US 9,457,153 B2
(45) Date of Patent: Oct. 4, 2016

(54) SYRINGE ACCESSORY

(71) Applicant: Vascular Insights LLC, Quincy, MA (US)

(72) Inventors: John P. Marano, Jr., Madison, CT (US); Stanley O. Thompson, New Boston, NH (US)

(73) Assignee: Vascular Insights LLC, Quincy, MA (US)

( * ) Notice: Subject to any disclaimer, the term of this patent is extended or adjusted under 35 U.S.C. 154(b) by 0 days.

(21) Appl. No.: 14/473,452

(22) Filed: Aug. 29, 2014

(65) Prior Publication Data

US 2016/0058953 A1    Mar. 3, 2016

(51) Int. Cl.
*A61M 5/00* (2006.01)
*A61M 5/315* (2006.01)

(52) U.S. Cl.
CPC ....... *A61M 5/31568* (2013.01); *A61M 5/3157* (2013.01); *A61M 5/31573* (2013.01); *A61M 2205/581* (2013.01); *A61M 2205/582* (2013.01); *A61M 2209/00* (2013.01)

(58) Field of Classification Search
CPC .............. A61M 5/3137; A61M 2005/3104; A61M 2005/3139
USPC ....................................... 604/207–211, 506
See application file for complete search history.

(56) References Cited

U.S. PATENT DOCUMENTS

| | | | |
|---|---|---|---|
| 145,217 A | 12/1873 | Leiter | |
| 2,943,624 A * | 7/1960 | Alquist | A61M 5/31555 604/210 |
| 4,466,426 A | 8/1984 | Blackman | |
| 4,642,102 A | 2/1987 | Ohmori | |
| 4,654,035 A | 3/1987 | Ando | |
| 5,733,258 A * | 3/1998 | Lane | A61M 5/31581 604/209 |
| 6,579,269 B1 * | 6/2003 | Kleyman | A61M 5/31555 604/207 |
| 7,611,495 B1 * | 11/2009 | Gianturco | A61M 5/31501 604/207 |
| 7,699,816 B2 | 4/2010 | Kirchhofer et al. | |
| 7,901,384 B2 | 3/2011 | Kleyman et al. | |
| 8,348,905 B2 | 1/2013 | Radmer et al. | |
| 2005/0055040 A1 | 3/2005 | Tal | |
| 2009/0270889 A1 | 10/2009 | Tal et al. | |
| 2010/0217306 A1 | 8/2010 | Raabe et al. | |
| 2010/0217313 A1 | 8/2010 | Raabe et al. | |
| 2011/0046565 A1 | 2/2011 | Radmer et al. | |
| 2011/0106018 A1 | 5/2011 | Rufer et al. | |
| 2011/0118701 A1 | 5/2011 | Baney et al. | |
| 2013/0096493 A1 | 4/2013 | Kubo et al. | |
| 2013/0197446 A1 | 8/2013 | Gustafsson et al. | |

FOREIGN PATENT DOCUMENTS

WO    WO 2011/064299 A1    6/2011

* cited by examiner

*Primary Examiner* — Phillip Gray
(74) *Attorney, Agent, or Firm* — Baker & Hostetler LLP

(57) ABSTRACT

Syringe devices and accessories for providing feedback to a user are disclosed.

24 Claims, 7 Drawing Sheets

SYRINGE ACCESSORY

SUMMARY

Syringe devices and accessories for providing feedback to a user are disclosed.

A syringe device or an accessory for a syringe may provide feedback, particularly audible and/or tactile feedback, to a user to communicate to the user that a predetermined amount of fluid (gas or liquid) has been dispensed from the syringe. The feedback may occur only once, indicating that one dose or bolus of a particular size has been dispensed. Or the feedback may repeat, indicating that successive quantities of fluid have been dispensed. For example, the feedback might occur only once, when an entire 5 milliliter bolus had been dispensed, or the feedback might occur repeatedly to indicate each milliliter of fluid dispensed.

Because most syringe barrels have a constant cross-sectional area along their length, the amount of fluid dispensed is usually directly proportional to the linear travel of the syringe plunger. Thus, in some embodiments the feedback is triggered by the linear travel of the syringe plunger. But the same concept of user-feedback could be implemented in a fluid dispenser for which the quantity of fluid dispensed is not proportional to the linear travel of a plunger or other actuator.

DETAILED DESCRIPTION

Figure 1:
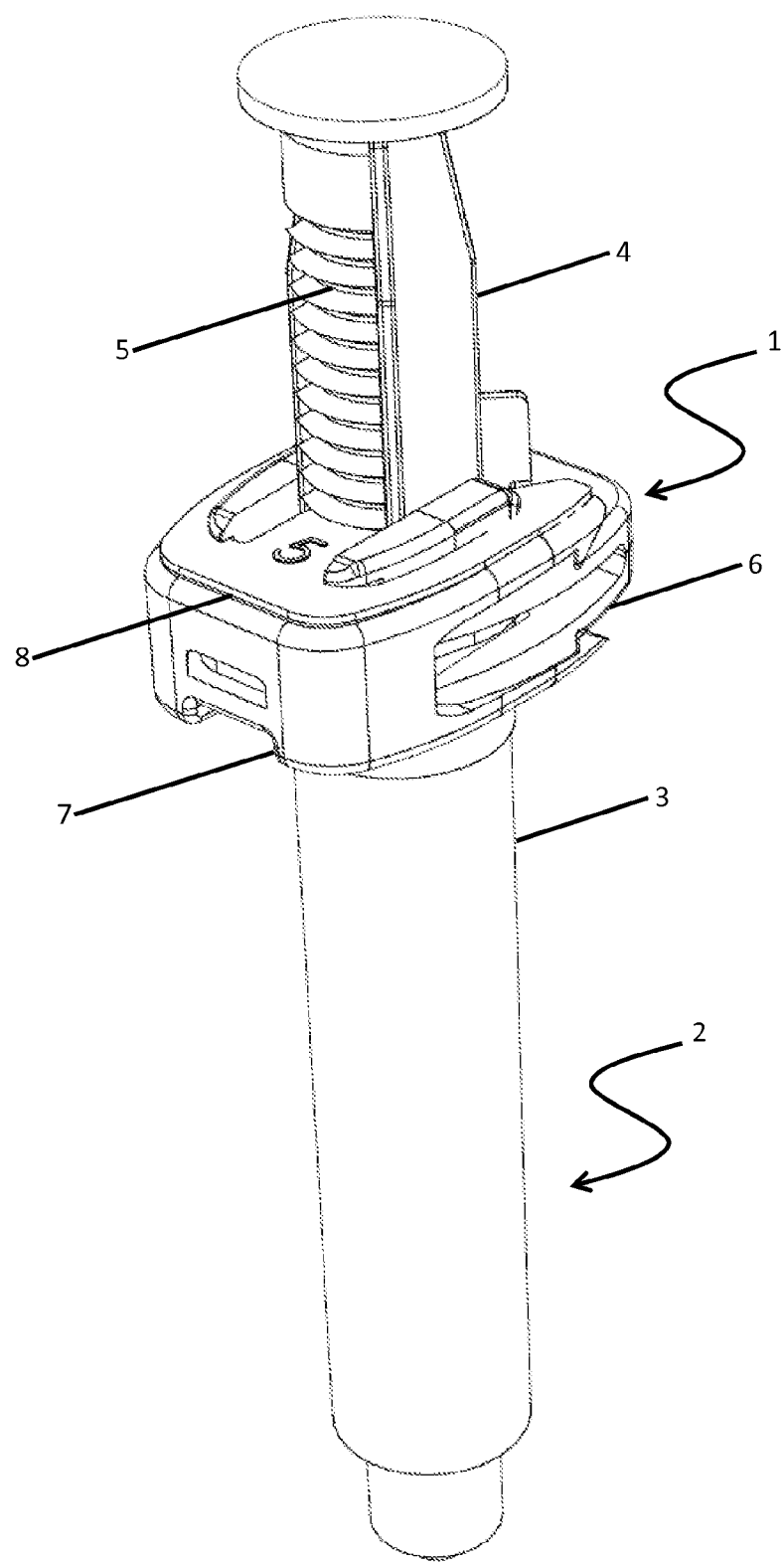
FIGS. 1-7 show schematically a particular embodiment of a syringe accessory for providing feedback to a user.
Figure 2:
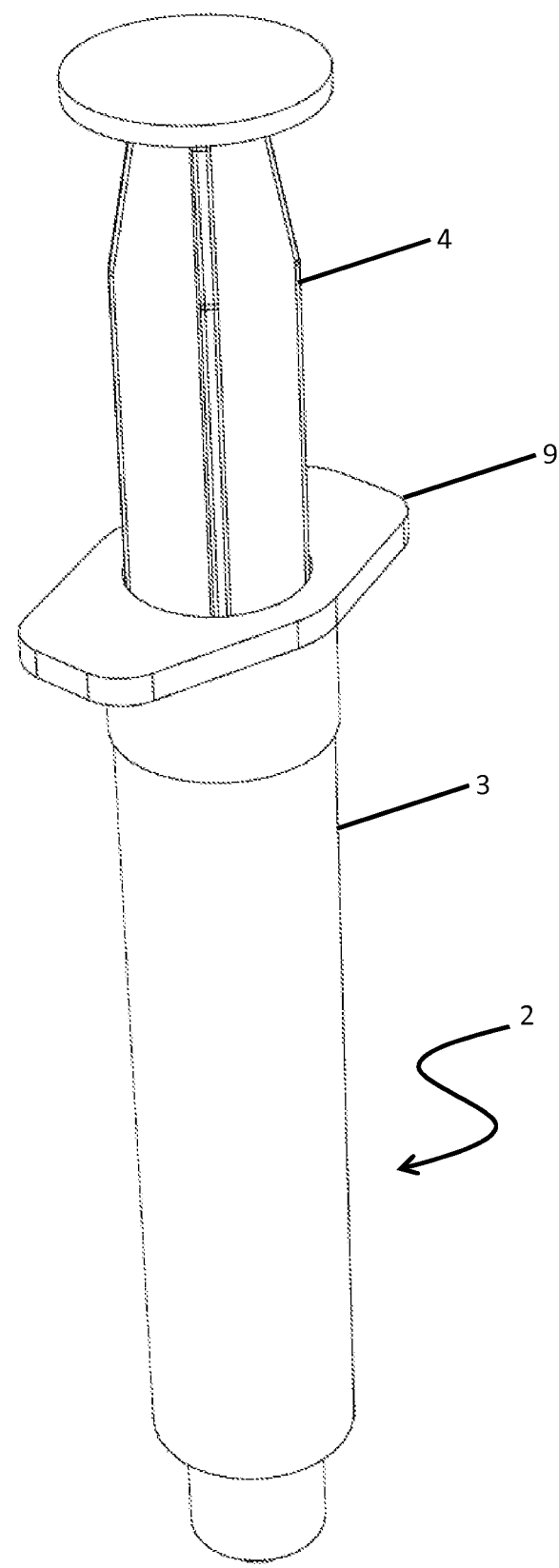
Figure 3:
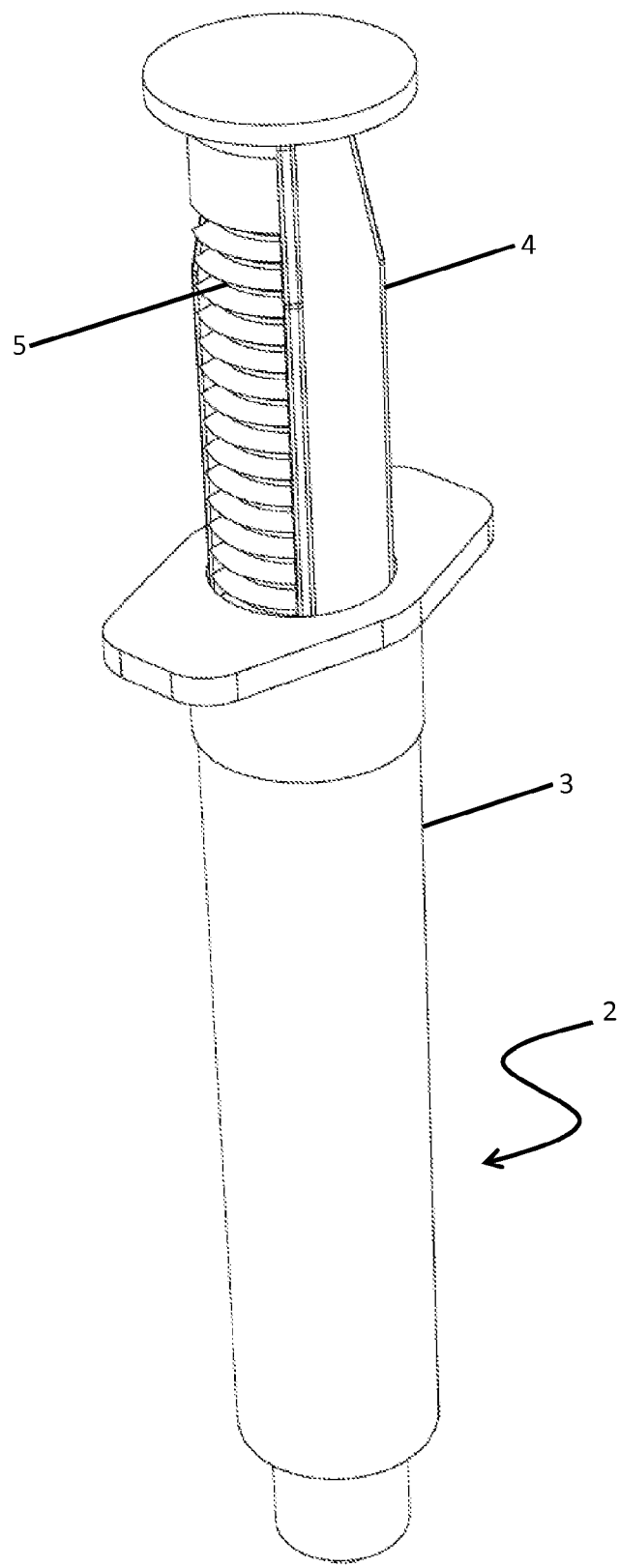

FIG. 1 schematically shows one particular embodiment of a syringe accessory 1 attached to a standard syringe 2. In this case, the figure shows a syringe that, by itself, includes no mechanism for providing auditory or tactile feedback to the user. For reference, FIG. 2 schematically shows the same standard syringe 2 with no part of the accessory included. The syringe 2 includes the usual barrel 3 and plunger 4. The barrel also includes a finger flange 9 that is obscured by other parts in the other figures.

The embodiment of the accessory 2 shown in the figures has generally two parts, a rack 5 and a housing. The housing in this embodiment has three parts, a base 6, a holder 7, and a membrane 8.

The rack 5 has a set of teeth along one side, and is designed to be affixed to the plunger on the side opposite the teeth. The rack 5 can be affixed to the plunger 4 by, for example, two snap-fit arms that mate with ribs on the plunger, although any of a wide variety of fixations could be employed. In such a version of the rack 5, the upper surface of the rack 5, including the upper surface of the arms, abuts the thumb rest, so that when the plunger 4 is advanced, the rack 5 advances as well. The rack 5 has a small enough profile that when the plunger 4 and rack 5 are advanced, the rack 5 fits inside the barrel 3 of the syringe behind the plunger seal. In addition to the two arms, the rack may include arms at the lower end that similarly affix the rack 5 to the plunger 4. Alternatively, the rack may be affixed to the plunger in any way that does not impair the function of the plunger or the rack, as described below. As shown in FIG. 1, the rack can be affixed to the plunger without removing the plunger from the barrel.

Figure 4:
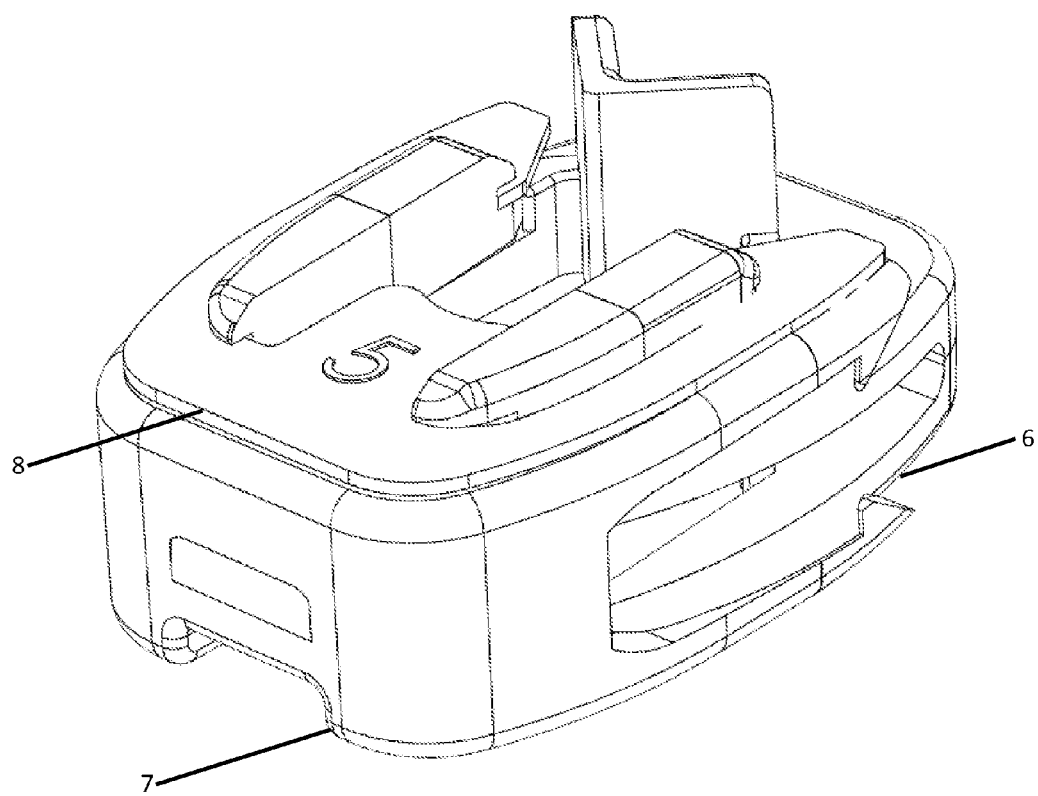
Figure 5:
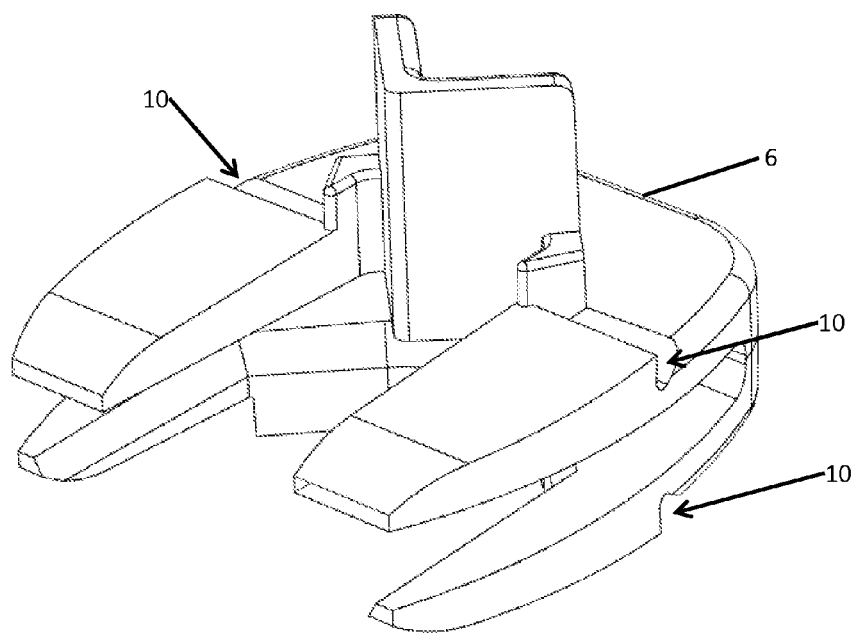
Figure 6:
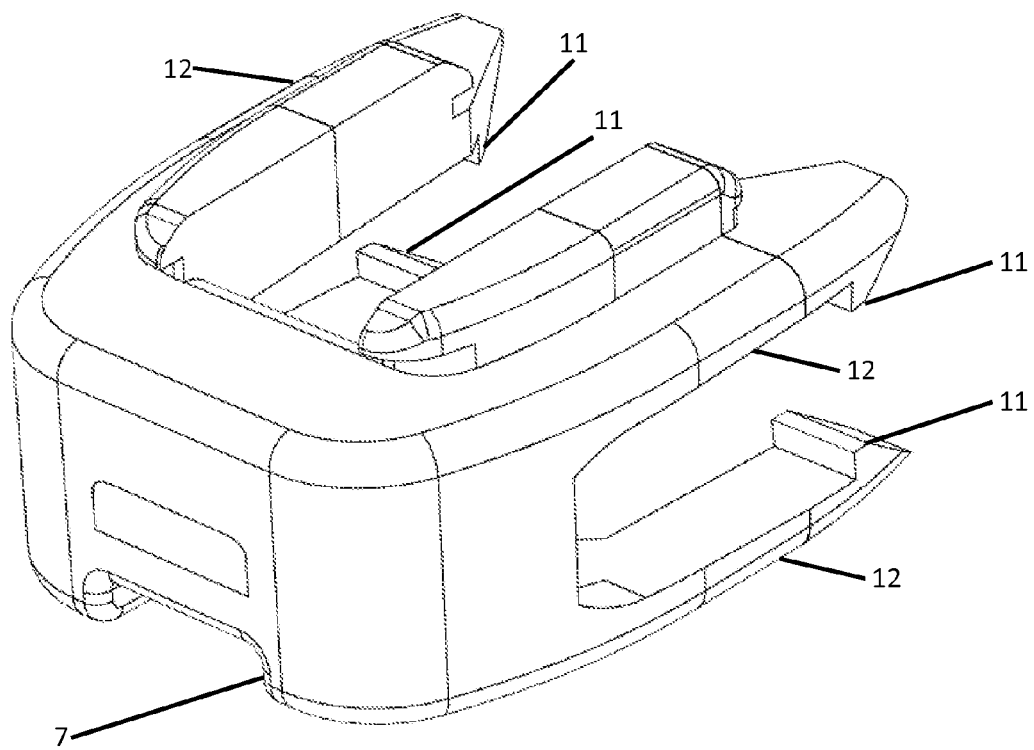
Figure 7:
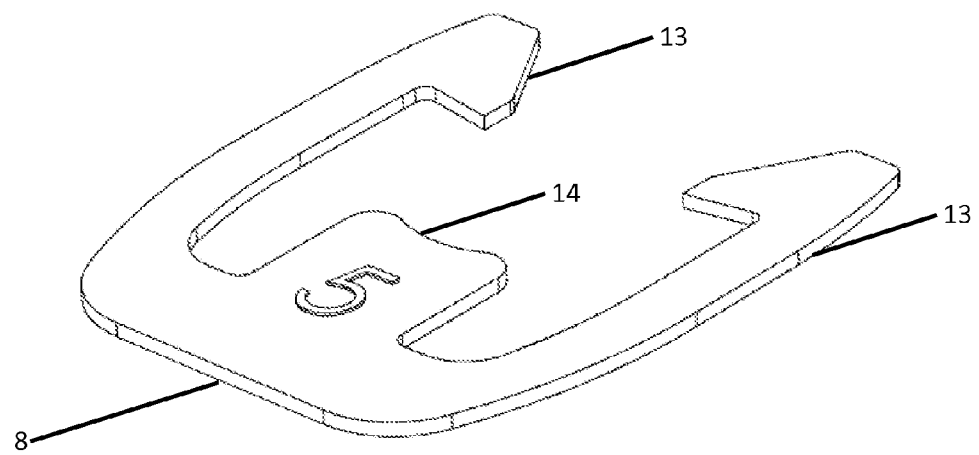

FIG. 1 also schematically shows the housing attached to the finger flange 9. As shown, the housing, shown in more detail in FIG. 4, includes two identical mating halves that snap together, a base 6 and a holder 7, shown in detail in FIG. 5 and FIG. 6 respectively.

The base 6 defines four receiving grooves 10, each sized and shaped to mate with a protrusion 11 formed at the end of an arm 12 of the holder 7. Once connected, the mating base 6 and holder 7 fit snugly around the finger flange 9 while leaving an opening large enough for the plunger 4 and rack 5 to pass through. The housing also includes a membrane 8, or flapper. As shown, the flapper 8 includes hooked arms 13 that secure it to the holder 7. Alternatively, as an example, the flapper 8 can define openings to be stretched over barbs protruding from the holder 7 that hold the flapper 8 in place on the holder 8. The flapper 8 defines a central opening that is generally large enough to allow free passage of the plunger and rack, except where a tongue 14 protrudes into the opening. The tongue 14 is sized and shaped to extend into a gap between neighboring teeth on the rack 5 while remaining in a relaxed state, if the gap between teeth is vertically aligned with the tongue 14. The tongue 14 is also long enough that, when the plunger is depressed, a downwardly moving tooth will flex the tongue 14 downward. When the tooth has moved far enough downward, the tongue 14 will snap upward into the next gap between teeth, so that the flapper 8 transitions back into its relaxed state. The same process applies to retracting the plunger rather than advancing it.

Depending on the material from which the flapper 8 is constructed, auditory and/or tactile feedback can be produced when the flapper transitions between the flexed and relaxed states. In a particular embodiment, the flapper is 0.015 inch thick polycarbonate. Such a flapper 8 has been found to produce a waveform that can easily be both heard and felt by a user when the flapper 8 transitions from flexed to relaxed. Other materials in other thicknesses and configurations may be used as well, including other plastics or metals, and may produce feedback when transitioning from flexed to relaxed, from relaxed to flexed, or both. All configurations that provide feedback to the user, such as auditory and/or tactile feedback, would suffice.

The interaction of the rack with the housing, in this case of the teeth with the flapper, is what provides feedback to the user. Thus the spacing of the teeth defines the information contained in the feedback. If the rack has a series of teeth with uniform vertical spacing, the feedback will indicate that the plunger has traveled uniform vertical steps. In a standard syringe having a barrel of constant cross-sectional area, this corresponds to uniform incremental dosages of the fluid dispensed from the syringe. Widely spaced teeth will give the user coarser information about the amount of fluid dispensed from the syringe. Closely spaced teeth will give the user information about smaller incremental dosages of fluid. In embodiments in which the teeth are spaced uniformly, the rhythm and tempo of the feedback can provide the user with information about the rate at which the fluid is being dispensed.

In some embodiments, the housing and rack are designed to create some, or little, or no, or substantially no impediment to moving the plunger relative to the barrel. In some embodiments, where the housing and rack provide no or substantially no impediment to moving the plunger relative to the barrel, a smooth motion of the plunger relative to the barrel will not be interrupted or impeded, despite the fact that the interaction of the housing with the rack is providing feedback to the user. In such embodiments, like the embodiment shown in FIG. 1, the flapper provides feedback as the flapper passes by a particular tooth, not when the flapper first encounters that particular tooth. In that embodiment, the feedback is generated by the flapper transitioning from flexed to relaxed. This is consistent with a more general class of embodiments in which the feedback is generated so as not to impede or substantially impede the motion of the plunger relative to the barrel.

The flapper can be die-cut, or waterjet-cut, or otherwise converted from the bulk sheet material. Alternatively, the flapper could be molded, e.g., injection molded, or made by any other process that results in an appropriately shaped part. As shown here, the flapper has a shape that engages with the barbs or other protrusions on the mating halves so that the flapper remains captured by the barbs of the housing after assembly. The relationship of the flapper to the rest of the housing allows a limited range of motion between the flapper and the mating halves without permitting any disengagement of the flapper from the mating halves. The flapper has a shape that permits momentary deviation from flatness to aid both its assembly to the rest of the housing and also the creation of a feedback waveform. Alternatively, the flapper could have any other shape that allows it to engage with the rest of the housing and still provide feedback.

As shown in FIG. 1, the plunger moves in a purely axial direction relative to the barrel and as a consequence, the rack moves in a purely axial direction relative to the housing. Motion of the plunger and/or rack relative to the barrel and/or housing is substantially restricted to motion in a single direction, generally along the axial direction of both the plunger and the barrel.

In other embodiments, a rack may be attached to plunger that interacts with the housing in a different way. For example, the housing could include a device for detecting light of a predetermined wavelength range, while the rack could include a pattern detectable in the predetermined wavelength range. The pattern could, for example be a bar-code-type pattern or other similar pattern. In another alternative, the housing and rack could define an electrical circuit whose properties change as the plunger is depressed. The rack and plunger could, for example, collectively form a variable circuit element like a potentiometer. Or the rack and plunger could interact by capacitive sensing. In any case, the sensed movement of the plunger relative to the barrel could then be translated into some sort of user feedback. Any interaction by which the motion of the plunger relative to the barrel is sensed could serve. Electronic or optical systems may be well suited to embodiments in which the interaction of the rack with the housing provides no, substantially no, or little, physical impediment to moving the plunger relative to the barrel.

One useful application of the syringe accessories described herein is in combination with a vascular treatment device, for example, as described in U.S. Pat. No. 7,967,834 and U.S. Pat. App. No. 2012/0109191, both of which are hereby incorporated herein by reference in their entirety. Such vascular treatments device may be used for ablating blood vessels, such as varicose veins, and for treating thrombosis by macerating a clot and injecting a thrombolytic drug, among other uses. A vascular treatment device may include a rotatable wire, so sized and shaped for ablating blood vessels, coupled to a cartridge that is engageable to a handle. The wire may thus be indirectly engaged with a motor in the handle such that the wire rotates when the motor is turned on. When the device is used for treating a varicose vein, the rotating wire may perturb the vessel to cause vasospasm, a condition in which blood vessels spasm, and may cause damage to the vessel wall to promote sclerosis. During a thrombectomy procedure, the wire may macerate a clot without causing damage to the vessel wall.

In some such vascular treatment devices, a reservoir connectable to the device may include a syringe having a plunger and a barrel. The syringe may be in fluid communication with a bore of a sheath of the device so as to be adapted for releasing a substance at the wire distal end, such as a sclerosant, an adhesive, a thrombolytic drug, streptokinase, or tissue plasminogen activator. In this manner the device may synergistically combine physical perturbation by the wire with drug treatment to improve device efficacy.

An accessory can be fitted to a syringe having a plunger and a barrel. The accessory can include a housing and a rack. The housing can be configured to attach to the barrel, while the rack is configured to attach to the plunger. The rack and housing can be configured so that when (a) the housing is attached to the syringe barrel and (b) the rack is attached to the syringe plunger and (c) a user advances the plunger into the barrel, then rack interacts with the housing thereby providing feedback to the user. In some embodiments, the rack interacts with the housing without substantially impeding the movement of the plunger relative to the barrel. The feedback can be, for example, auditory or tactile.

The housing may include a flapper. The rack may interact with the housing by transitioning the flapper between a relaxed state and a flexed state. The rack can include one or more ridges or teeth. The teeth can be configured so that each tooth transitions the flapper between a relaxed state and flexed state at a given vertical position of the rack and/or plunger relative to the barrel. The flapper can be configured such that when the flapper is positioned between two teeth, the flapper transitions from a flexed state to a relaxed state. The rack may include a series of such teeth which may be evenly spaced along the rack such that when a user advances the plunger into the barrel, the flapper interacts sequentially with each tooth in the series, and such that when the flapper is positioned between any two adjacent teeth, the flapper transitions from a flexed state to a relaxed state.

Transitioning the flapper between a relaxed state and a flexed state may present substantially no resistance to the advancement of the plunger relative to the barrel.

The flapper may provide feedback when the flapper transitions from a relaxed state to a flexed state, or when the flapper transitions from a flexed state to a relaxed state, or both when the flapper transitions from a relaxed state to a flexed state and when the flapper transitions from a flexed state to a relaxed state.

The flapper may be sized and shaped so that transitioning the flapper between a relaxed state and a flexed state generates a waveform capable of auditory or tactile detection by a human operator. The flapper may be about 0.015 inches think in its smallest dimension.

In some embodiments, the rack interacts with the housing electronically or optically.

In some embodiments, the rack and housing are configured so that, when (a) the housing is attached to the syringe barrel, and (b) the rack is attached to the syringe plunger, and (c) a user advances the plunger into the barrel, then the housing does not directly contact the plunger.

A kit can include a syringe having a plunger and a barrel and a syringe accessory as described above. Such a kit can be assembled into a syringe accessory wherein the plunger is at least partially disposed within the barrel, the housing is attached to the barrel, and the rack is attached to the plunger.

We claim:

1. An accessory for a syringe having a plunger and a barrel, the accessory comprising:
a housing configured to removably attach to the barrel, the housing including a holder and a base removably attached to the holder along a first direction, wherein the holder and the base define a housing channel that is elongate through the housing along a second direction, the second direction being substantially perpendicular to the first direction; and
a rack configured to removably attach to the plunger, at least a portion of the rack and the plunger being moveably disposed within the housing channel, the rack further configured to intermittently contact the housing as the plunger is pressed into the barrel, wherein a number of intermittent contacts between the housing and the rack is providing a feedback indicative of a distance the plunger has traveled relative to the barrel.

2. The syringe accessory of claim 1, wherein the feedback comprises auditory feedback.

3. The syringe accessory of claim 1, wherein the feedback comprises tactile feedback.

4. The syringe accessory of claim 1, wherein:
the housing comprises a flapper; and
the rack and flapper are configured to intermittently contact, thereby transitioning the flapper between a relaxed state and a flexed state.

5. The syringe accessory of claim 4, wherein:
the rack comprises at least one tooth;
each tooth is configured to intermittently contact the flapper, thereby transitioning the flapper between the relaxed state and the flexed state.

6. The syringe accessory of claim 4, wherein:
the rack comprises:
a first of a plurality of teeth configured to intermittently contact the flapper, thereby transitioning the flapper between the relaxed state and the flexed state at a predetermined position of the plunger in the barrel; and
a second of the plurality of teeth adjacent to the first of the plurality of teeth, the second plurality of teeth configured to intermittently contact the flapper, thereby transitioning the flapper between the relaxed state and the flexed state at a different predetermined position of the plunger in the barrel than the first of the plurality of teeth;
the rack being configured such that when the flapper interacts with the first of the plurality of teeth and before it interacts with the second of the plurality of teeth, the flapper transitions from the flexed state to the relaxed state.

7. The syringe accessory of claim 4, wherein:
the rack comprises a series of teeth;
when a user advances the plunger into the barrel, the flapper interacts sequentially with each tooth in the series; and
when the flapper is positioned between any two adjacent teeth, the flapper transitions from the flexed state to the relaxed state.

8. The syringe accessory of claim 4, wherein the rack and housing are configured so that, when:
the plunger is advanced along the second direction into the barrel, transitioning the flapper between the relaxed state and the flexed state presents substantially no resistance to the advancement of the plunger relative to the barrel.

9. The syringe accessory of claim 4, wherein the flapper provides audible or tactile feedback when:
the flapper transitions from the relaxed state to the flexed state;
the flapper transitions from the flexed state to the relaxed state; or
both when the flapper transitions from the relaxed state to the flexed state and when the flapper transitions from the flexed state to the relaxed state.

10. The syringe accessory of claim 4, wherein the flapper is sized and shaped so that transitioning the flapper between the relaxed state and the flexed state generates a waveform capable of auditory or tactile detection by a human operator.

11. The syringe accessory of claim 4, wherein the flapper is about 0.015 inches thick in its smallest dimension.

12. The syringe accessory of claim 1, wherein the rack and housing are configured so that, when:
the plunger is advanced along the second direction into the barrel;
the housing does not directly contact the plunger.

13. The syringe accessory of claim 1, wherein the rack interacts with the housing electronically or optically.

14. A kit comprising:
a syringe having a plunger and a barrel; and
the syringe accessory of claim 1.

15. A syringe assembly assembled from the kit of claim 14, wherein:
the plunger is at least partially disposed within the barrel.

16. The syringe accessory of claim 1, wherein the rack interacts with the housing optically.

17. An accessory for a syringe having a barrel and a plunger, the accessory configured to provide feedback that a predetermined amount of gas or liquid has been dispensed from the syringe, the accessory comprising:
a housing configured to mount on the barrel of the syringe, the housing comprising:
a holder including a sidewall and at least one arm that extends from the sidewall in a first direction, the at least one arm having a protrusion, and
a base removably secured to the holder, the base defining at least one groove configured to mate with the protrusion on the at least one arm, respectively,
wherein the housing and the base together define a housing channel elongate in a second direction, the housing channel configured to fit the barrel of the syringe within; and
a rack configured to mount on the plunger of the syringe, the rack further configured to intermittently contact a portion of the housing as the plunger is pressed into the barrel.

18. The accessory of claim 17, wherein the second direction is substantially perpendicular to the first direction.

19. The accessory of claim 17, wherein the housing further includes a flapper, the flapper having a tongue that extends at least partially in the first direction into the housing channel and is configured to intermittently contact the rack.

20. The accessory of claim 19, wherein the rack includes a plurality of teeth, and wherein each of the plurality of teeth is configured to intermittently contact the flapper as the plunger is advanced along into the barrel.

21. The accessory of claim 19, wherein the flapper is removably attached to the holder and defines a portion of the housing channel.

22. The accessory of claim 21, wherein the flapper further includes at least one hooked arm configured to secure the flapper to the holder.

23. A method for using a syringe having a plunger and a barrel, the method comprising:

dispensing a fluid from the syringe by advancing the plunger into the barrel in a first direction, the barrel having a housing removably coupled thereto, the housing including a holder and a base removably attached to the holder along a second direction, wherein the holder and the base define a housing channel that is elongate through the housing along the first direction, the first direction being substantially perpendicular to the second direction; and indicating a rate at which the fluid is dispensed from the syringe by an auditory feedback, the plunger having a rack removably coupled thereto, wherein at least a portion of the rack and the plunger are moveably disposed within the housing channel, the rack being configured to intermittently contact the housing as the plunger is advanced into the barrel.

24. The method of claim 23, further comprising:

adjusting the rate at which fluid is dispensed from the syringe based on the auditory feedback.

\* \* \* \* \*